(12) United States Patent
Shaligram et al.

(10) Patent No.: US 10,266,654 B2
(45) Date of Patent: Apr. 23, 2019

(54) POLY-BENZIMIDAZOLE WITH PYRENE AND ANTHRACENE FLOUROPHORE

(71) Applicant: Council of Scientific & Industrial Research, New Delhi (IN)

(72) Inventors: Sayali Vinayak Shaligram, Maharashtra (IN); Ulhas Kanhaiyalal Kharul, Maharashtra (IN); Prakash Purushottam Wadgaonkar, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 93 days.

(21) Appl. No.: 15/122,126

(22) PCT Filed: Feb. 27, 2015

(86) PCT No.: PCT/IN2015/050013
§ 371 (c)(1),
(2) Date: Aug. 26, 2016

(87) PCT Pub. No.: WO2015/128884
PCT Pub. Date: Sep. 3, 2015

(65) Prior Publication Data
US 2016/0369057 A1 Dec. 22, 2016

(30) Foreign Application Priority Data
Feb. 27, 2014 (IN) .......................... 0552/DEL/2014

(51) Int. Cl.
*G01N 33/22* (2006.01)
*C08G 73/18* (2006.01)
(Continued)

(52) U.S. Cl.
CPC ........... *C08G 73/18* (2013.01); *B01D 53/228* (2013.01); *B01D 71/58* (2013.01); *B01J 20/265* (2013.01);
(Continued)

(58) Field of Classification Search
CPC ....... G01N 33/227; C08G 73/18; C08L 79/04; C08L 2203/16; B01J 20/265; B01J 20/3085; B01D 53/228; B01D 71/58
See application file for complete search history.

(56) References Cited

U.S. PATENT DOCUMENTS 5,856,384 A    1/1999  Garito et al.
5,902,876 A *  5/1999  Murata ................. C08G 73/18
                                          528/125

FOREIGN PATENT DOCUMENTS

EP              2003123 A2    12/2008
WO    WO-2012035556 A1 *  3/2012  ............ C08G 73/18
WO       WO 2015/128884 A1     9/2015

OTHER PUBLICATIONS

Birks, J. B. et al. "The fluorescence excitation spectra of aromatic liquids and solutions." J. Phys. B (1968) 1 934-945. (Year: 1968).*
(Continued)

*Primary Examiner* — Christopher Adam Hixson
(74) *Attorney, Agent, or Firm* — Knobbe, Martens, Olson & Bear, LLP

(57) ABSTRACT

The present invention discloses polymeric ionic liquid (PIL) composition comprising a polymer selected from PBI or ABPBI and their derivatives or analogues covalently attached to fluorescence moiety selected from poly aromatic hydrocarbons, preferably pyrene or anthracene. Further, the invention discloses a process for preparing said composition with enhanced fluorescence and stability. Also, disclosed herein is the use of said fluorescent PIL in detection of explosives, as membranes for gas permeation and as chemo sensors.

11 Claims, 7 Drawing Sheets

(51) Int. Cl.
  C08L 79/04     (2006.01)
  B01J 20/26     (2006.01)
  B01J 20/28     (2006.01)
  B01J 20/30     (2006.01)
  B01D 71/58     (2006.01)
  B01D 53/22     (2006.01)

(52) U.S. Cl.
  CPC ..... B01J 20/28011 (2013.01); B01J 20/3078 (2013.01); B01J 20/3085 (2013.01); C08L 79/04 (2013.01); G01N 33/227 (2013.01); *C08L 2203/16* (2013.01)

(56) References Cited

OTHER PUBLICATIONS

Jing et al., "Fluorescent probe for Fe(III) based on pyrene grafted multiwalled carbon nanotubes by click reaction", Analyst, 137:1718-1722 (2012).
He et al., "Pyrene-Containing Conjugated Polymer-Based Fluorescent Films for Highly Sensitive and Selective Sensing of TNT in Aqueous Medium", Macromolecules, 44:4759-4766 (2011).
Bai et al., "Pyrenyl Excimers Induced by the Crystallization of POSS Moieties: Spectroscopic Studies and Sensing Applications", ChemPhysChem, 9:1908-1913 (2008).
Kumar et al., "Optical properties of pyrene and anthracene containing imidazoles: Experimental and theoretical investigations", Journal of Photochemistry and Photobiology A: Chemistry, 218:162-173 (2011).
Ding, et al., "A single fluorescent self-assembled monolayer film sensor with discriminatory Power" *Journal of Materials Chemistry*, vol. 22, 2012, pp. 11574-11582.
Han, et al., "Synthesis and Characterization of Fluorene-Based Polybenzimidazole Copolymer for Gas Separation" *Journal of Applied Polymer Science*, 2014, pp. 1-9.
Kumar, et al., "Optical properties of pyrene and anthracene containing imidazoles: Experimental and theoretical investigations" *Journal of Photochemistry and Photobiology A: Chemistry*, vol. 218, 2011, pp. 162-173.
Kumbharkar, et al., "Film forming polymeric ionic liquids (PILs) based on polybenzimidazoles for CO2 separation" *RSC Advances*, vol. 4, 2014, pp. 4500-4503.
Kumbharkar, et al., "N-substitution of polybenzimdazoles: Synthesis and evaluation of physical properties" *European Polymer Journal*, vol. 45, 2009, pp. 3363-3371.
Shaligram, et al., "Fluorescent polymeric ionic liquids for the detection of nitroaromatic explosives" *Journal of Materials Chemistry A*, vol. 2, 2014, pp. 13983-13989.
International Search Report for International Application No. PCT/IN2015/050013 dated Sep. 10, 2015.
Written Opinion of International Searching Authority in application No. PCT/IN2015/050013 dated Sep. 10, 2015.
International Preliminary Report on Patentability issued in application No. PCT/IN2015/050013 dated Feb. 26, 2016.

* cited by examiner

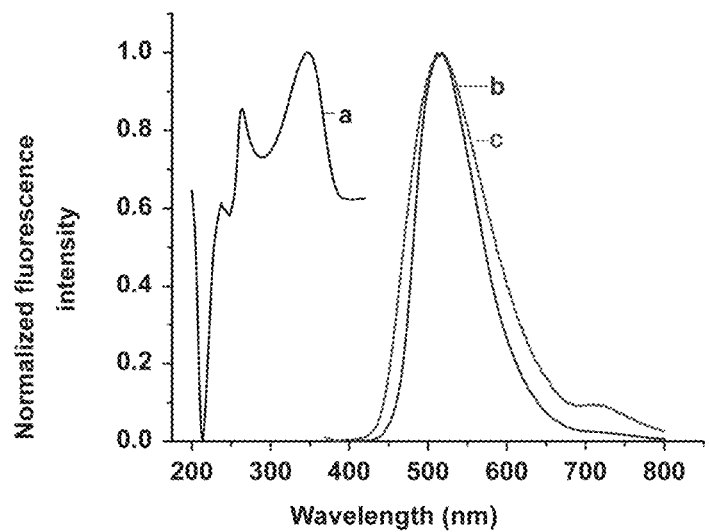
Fig: 1
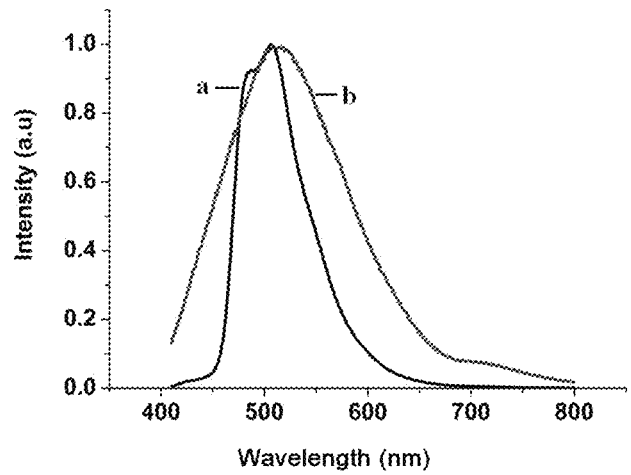
Fig: 2

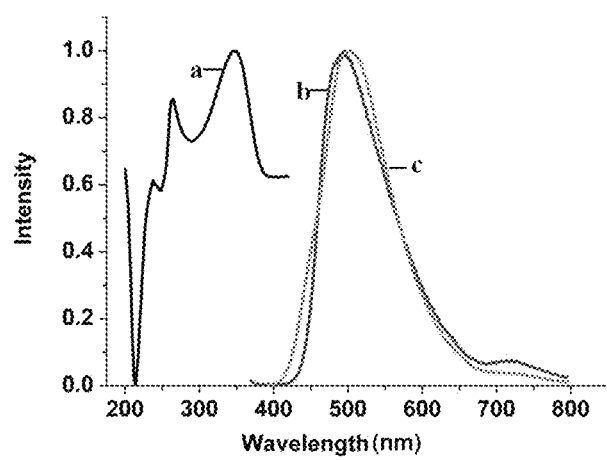
Fig: 3
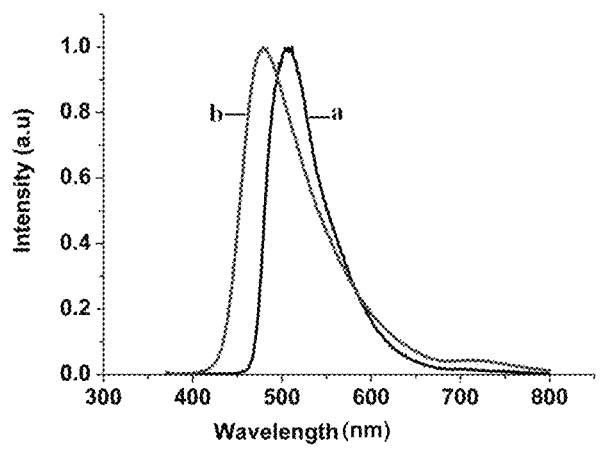
Fig: 4

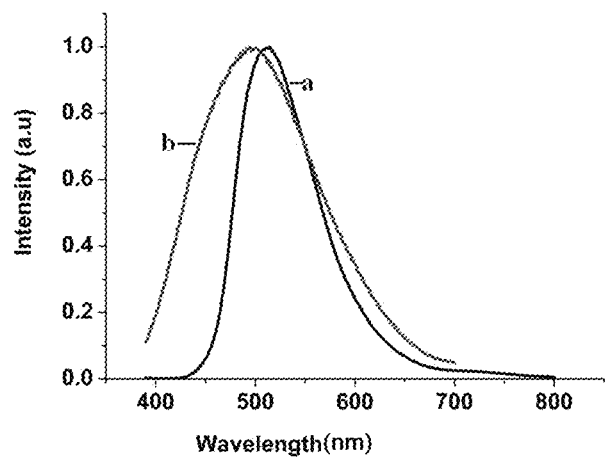
Fig: 5
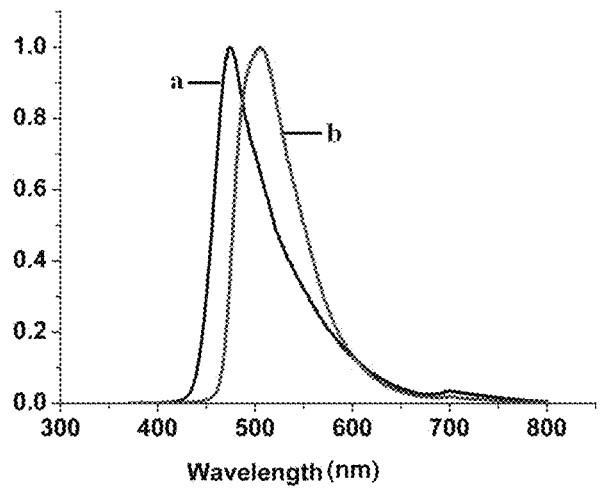
Fig: 6

US 10,266,654 B2

POLY-BENZIMIDAZOLE WITH PYRENE AND ANTHRACENE FLOUROPHORE

This application is the U.S. National Phase under 35 U.S.C. § 371 of International Application No. PCT/IN2015/050013, filed Feb. 27, 2015, designating the U.S., and published in English as WO 2015/128884 A1 on Sep. 3, 2015, which claims priority to Indian Patent Application No. 0552/DEL/2014, filed Feb. 27, 2014, the entire contents of which are incorporated herein by reference.

FIELD OF THE INVENTION

The present invention relates to a polymeric ionic liquid (PIL) composition comprising polymers selected from Poly-benzimidazole (PBI) or ABPBI [AB (Polybenzimidazole) or phosphoric acid doped PBI] and their derivatives or analogues covalently attached to various fluorescent moieties selected from polyaromatic hydrocarbons, preferably pyrene or anthracene. Particularly, present invention relates to a process for preparing the said composition with enhanced fluorescence and stability. More particularly, present invention relates to the use of said fluorescent composition in detection of explosives, as membranes for gas permeation and as chemo sensors.

BACKGROUND OF THE INVENTION

Fluorescent technique is widely used among others in chemical, biochemical, medical, chemical research fields for analyzing organic compounds, detection of particular compounds in a complex, differentiating malignant cell from benign, with exquisite sensitivity and selectivity.

Fluorescent technique is now extended to develop photo luminescent devices for detecting explosives, in heavy chemical industry, mines, etc. such as sensing gas leakages and as chemo sensors and the like.

Article titled, "Fluorescent probe for Fe(III) based on pyrene grafted multiwalled carbon nanotubes by click reaction" by Li Jing, Cong Liang, Xinhao Shi, Siqiu Ye and Yuezhong Xian in *Analyst*, 2012,137, 1718-1722 reports the covalent functionalization of multiwalled carbon nanotubes (MWCNTs) with pyrene via Cu(I)-catalysed azide/alkyne click (CuAAC) reactions under mild conditions to afford the nano composites of pyrene-MWCNTs. Fourier transform infrared spectroscopy (FT-IR), ultraviolet and visible spectroscopy (UV-Vis), and fluorescence spectroscopy were used to characterize the nano composites of pyrene clicked MWCNTs. The nano composites of pyrene clicked MWCNTs are used in photo luminescent devices as a highly sensitive and selective fluorescence "turn-off" sensor for $Fe^{3+}$. Article titled "Pyrene-Containing Conjugated Polymer-Based Fluorescent Films for Highly Sensitive and Selective Sensing of TNT in Aqueous Medium" by Gang He, Ni Yan, Jiayu Yang, Hongyue Wang, Liping Ding, Shiwei Yin, and Yu Fang in Macromolecules, 2011, 44 (12), pp 4759-4766 reports the synthesis and characterization of two poly(pyrene-co-phenylene ethynylene)s of different compositions (PyPE-1 and PyPE-2). The two polymers were casted, separately, onto glass plate surfaces to fabricate films (film 1, film 2) for sensing performance studies. The fluorescence emissions of the two films were observed to be sensitive to the presence of 2,4,6-trinitrotoluene (TNT) in aqueous phase, however, TNT showed little effect upon the emission of the parent polymer, poly(phenyleneethynylene) (PPE). The difference was accounted for (1) the π-π interaction between pyrene moieties contained in the copolymers and the analyte, TNT, molecules, and (2) more suitable matching of the LUMOs (lowest unoccupied molecular orbital) of the pyrene-containing conjugated polymers with that of TNT molecules. Further experiments demonstrated that the sensing is reversible and rarely encounters interference from commonly found compounds, including other nitroaromatics (NACs). Fluorescence lifetime measurements revealed that the quenching is static in nature.

Article titled 'Pyrenyl Excimers Induced by the Crystallization of POSS Moieties: Spectroscopic Studies and Sensing Applications' by Hua Bai, Chun Li et. al in ChemPhysChem 2008, 9, 1908-1913; DOI: 10.1002/cphc.200800149 reports fluorescent sensors based on thin PBPOSS films for the rapid detection of TNT. The spin-coated thin films of PBPOSS emit strong blue light at 475 nm when excited at 350 nm because of the formation of a high content pyrenyl excimers induced by the crystallization of POSS moieties. As PBPOSS being small molecule, it cannot however form self-standing film.

Article titled 'Optical properties of pyrene and anthracene containing imidazoles:Experimental and theoretical investigations' by Dhirendra Kumar, K. R. Justin Thomas published in Journal of Photochemistry and Photobiology A: Chemistry 218 (2011) 162-173 reports a series of imidazole derivatives containing anthracene and pyrene segments useful to design imidazole dyes with higher wavelength absorptions for photovoltaic applications. The imidazole derivatives containing anthracene and pyrene segments show red-shifted absorption and emission profiles due to extended conjugation. The article does not disclose the use of polymer film possessing pyrene and anthracene fluorophores for the detection of nitroaromatics (NACs).

Article titled 'Pyrene-Containing Conjugated Polymer-Based Fluorescent Films for Highly Sensitive and Selective Sensing of TNT in Aqueous Medium' by Gang He, Ni Yan et al published in Macromolecules, 2011, 44 (12), pp 4759-4766 relates to two poly(pyrene-co-phenyleneethynylene)s of different compositions (PyPE-1 and PyPE-2) for sensing performance studies. The fluorescence emissions of the two films were sensitive to the presence of 2,4,6-trinitrotoluene (TNT). The thin films of polymer were fabricated by spin-coating technique which may not be self-standing; further the sensing was demonstrated in solution (aqueous phase).

In light of the potential applicability of fluorophores in photoluminescent devices as a highly sensitive and selective fluorescence, there remains a need in the art to provide composition with enhanced photoluminescence by coupling them with highly-conjugated polymer having bright luminescence and bipolar transport characteristics. Thin-film sensors are widely acceptable due to reusability and ease in device making. Therefore, thin films possessing excimer emission are very promising materials as fluorescence sensors.

However, preparation of self-standing polymeric ionic liquid (PIL) thin films with strong excimer emission is challenging as many factors exert influences on fluorescence properties of the fluorophores such as biomolecular structures, proximity and concentrations of quenching species, pH of the solvent, stability etc. Further, physical entrapment of the fluorescent probe in a polymer matrix produces inhomogeneity in the material and leads to stability issues due to the leaching of the fluorescent probe, reducing the lifetime and reproducibility of the sensor. The most preferred method to prevent decay of excimer emission is the covalent attachment of fluorophore in the polymer matrix.

Polymers such as Polybenzimidazole (PBI) or ABPBI are known for their rigidity, thermo-chemical and mechanical stability. The promising properties of these polymers render them suitable for incorporating fluorophores which can prevent decay of excimer emission during covalent attachment to flurophore in polymer matrix due to rigid backbone and bipolar transport characteristics.

Furthermore, polymeric materials exhibiting high $CO_2$ sorption are known in the art as sorbent and gas separation membrane material.

There is a publication, WO2012035556, of the present applicant which discloses Polybenzimidazole (PBI) based polymeric forms of ionic liquids as $CO_2$ sorbent and gas separation membrane materials, however does not disclose the fluorescent property and applicability for detecting explosives.

In light of the above, the present inventors felt a need to provide stable polymeric form of ionic liquid composition that possesses both enhanced fluorescence useful in detection of explosives and high degree of gas permeation capacity.

OBJECTIVE OF THE INVENTION

Main object of the present invention is to provide polymeric ionic liquid (PIL) composition comprising polymer selected from PBI or ABPBI and its derivatives or analogues thereof covalently attached to polyaromatic hydrocarbons that possesses enhanced fluorescence useful in detection of explosives and also possess high degree of gas permeation capacity.

Yet another object of the present invention is to provide a process for the preparation of said composition.

SUMMARY OF THE INVENTION

Accordingly, present invention provides a stable polymeric ionic liquid (PIL) composition comprising polymer selected from PBI or ABPBI and derivatives or analogues thereof covalently attached to fluorescing moiety selected from poly aromatic hydrocarbons.

In an embodiment of the present invention, the poly aromatic hydrocarbons are selected from the group consisting of coronene, perylene, anthracene, phenanthrene, chrysene, pentacene, pentaphene, tetraphene, naphthalene, ovalene, rubrene, pyrene and the like.

In another embodiment of the present invention, the poly aromatic hydrocarbons are preferably pyrene or anthracene.

In yet another embodiment of the present invention, said composition is selected from;
i. PBI-BuI;
ii. [DAnDBzPBI-BuI][Br] comprising PBI-BuI disubstituted with anthryl group quaternized with 4-tert-butyl-benzyl bromide;
iii. [DPyDBzPBI-BuI][Br] comprising PBI-BuI disubstituted with pyrenyl group quaternized with 4-tert-butyl-benzyl bromide;
iv. [DAnPBI-BuI][Br] comprising PBI-BuI disubstituted with anthryl group;
v. [DPyPBI-BuI][Br] comprising PBI-BuI disubstituted with pyrenyl group;
vi. [DPyDBzPBI-I][Br] comprising PBI-I disubstituted with pyrenyl group quaternized with 4-tert-butylbenzyl bromide;
vii. [DAnPBI-I] comprising PBI-I disubstituted with anthryl group;
viii. [DPyPBI-I] comprising PBI-BuI disubstituted with pyrenyl group;
ix. [AnBzABPBI][Br] comprising ABPBI substituted with anthryl group and quaternized with 4-tert-butylbenzyl bromide;
x. [PyBzABPBI][Br] comprising ABPBI substituted with pyrenyl group and quaternized with 4-tert-butylbenzyl bromide;
xi. [AnABPBI] comprising ABPBI substituted with anthryl group;
xii. [PyABPBI] comprising ABPBI substituted with pyrenyl group; and
xiii. [DAnDBzPBI-I][Br] comprising PBI-I disubstituted with anthryl group quaternized with 4-tert-butyl benzyl bromide In yet another embodiment of the present invention, said composition is in the form of self-standing film.

In yet another embodiment, present invention provides a process for the preparation of stable PIL composition according to claim 1, comprising the steps of;
a. preparing metal salt of PBI or ABPBI and its derivatives or their analogues in dry solvent by known method followed by adding metal hydride to obtain a mixture;
b. heating the reaction mixture as obtained in step (a) at a temperature of about 80° C. until complete dissolution of polymer;
c. cooling the solution as obtained in step (b) followed by adding drop wise aralkyl halide of polyaromatic hydrocarbon dissolved in dry solvent to obtain precipitate of PIL composition.

In yet another embodiment of the present invention, the process comprises N-quaternization of N-substituted PBI or ABPBI and its derivatives or their analogues of step (c) with (un)substituted or substituted alkyl/aryl halides.

In yet another embodiment of the present invention, the poly aromatic hydrocarbons are selected from coronene, perylene, anthracene, phenanthrene, chrysene, pentacene, pentaphene, tetraphene, naphthalene, ovalene, rubrene, pyrene and the like.

In yet another embodiment of the present invention, the poly aromatic hydrocarbons are pyrene or anthracene.

In yet another embodiment of the present invention, said composition is useful as explosive sensors, chemo sensors and as membranes in gas permeations.

BRIEF DESCRIPTION OF THE DRAWINGS

FIG. 1 Fluorescence emission of a: PBI-BuI, b: [DPyD-BzPBI-BuI][Br] and c: [DAnDBzPBI-BuI][Br].

FIG. 2 Fluorescence emission of a: [DAnDPBI-BuI]and b: [DPyPBI-BuI]

FIG. 3 Fluorescence emission of a: PBI-I, b: [DAnDBz-PBI-I][Br] and c: [DPyDBzPBI-I][Br]

FIG. 4 Fluorescence emission of a: [DAnPBI-I] and b: [DPyPBI-I]

FIG. 5 Fluorescence emission of a: [AnBzABPBI][Br] and b: [PyBzABPBI][Br]

FIG. 6 Fluorescence emission of a: [AnABPBI] and b: [PyABPBI]

DETAILED DESCRIPTION OF THE INVENTION

Figure 7:
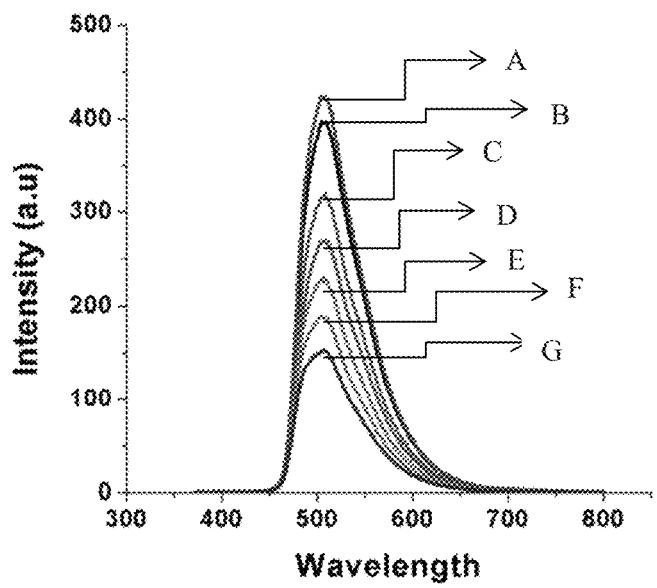
FIG. 7 depict Fluorescence emission spectra of [DPyD-BzPBI-I][Br] in the presence of different concentrations of nitrobenzene (from top to bottom: 0, 15, 30, 45, 60, 75 and 90 μM; A to G respectively) in DMSO (λex=350 nm).

Present invention provides a stable polymeric ionic liquid (PIL) composition comprising polymer selected from PBI or ABPBI and its derivatives or analogues thereof covalently attached to fluorescent moiety selected from polyaromatic hydrocarbons.

The polyaromatic hydrocarbons are selected from coronene, perylene, pyrene, anthracene, phenanthrene, chrysene, pentacene, pentaphene, tetraphene, naphthalene, ovalene, rubrene and the like; preferably pyrene or anthracene.

The fluorescent PIL composition is stable and is in the form of self-standing films due to covalent bonding of fluorophore such as pyrene and anthracene in PILs and the rigid polymer PBI or ABPBI and its derivatives or analogues.

The self-standing films is in the range of 5 μm-250 μm thick.

The PIL composition exhibits enhanced fluorescence in comparison to pyrene or anthracene as fluorophores alone.

The stable, self-standing fluorescent PIL film of the present invention exhibits fluorescence enhancement by excimer emission and fluorescence quenching. The sensing is demonstrated both in solution state as well as in vapor phase.

The self-standing fluorescent PIL film composition of the present invention has high permeability coefficient and selectivity for the gases selected from He, $H_2$, $N_2$, $CO_2$ and $CH_4$.

The self-standing fluorescent PIL film composition of the present invention finds applicability in devices for detecting explosives, as chemo sensors and as membranes useful in gas permeation.

The present invention provide a process for synthesis of fluorescent polymeric ionic liquid (PIL) composition via post modification of thermo-chemically and mechanically stable polybenzimidazole (PBI) or ABPBI and its derivatives or analogues thereof.

The process for synthesis consists of following steps:
  a) preparing metal salt of PBI or ABPBI and its derivatives or their analogues in dry solvent by adding metal hydride; heating the reaction mixture to a temperature of about 80° C. until complete dissolution of polymer occurs;
  b) cooling the solution followed by drop wise addition of adequate amount of alkyl/aryl halide of polyaromatic hydrocarbon dissolved in dry solvent to the mixture of step (a) to obtain precipitate of N-substituted PBI or ABPBI and its derivatives or their analogues.

The process of present invention further comprises N-quaternization of N-substituted PBI or ABPBI and its derivatives or their analogues. The N-quaternization is effected using (un)substituted or substituted alkyl/aryl halides. The degree of N-quarternization is in the range of 1% to 100%.

The process is depicted in Scheme 1 below:

Scheme 1: Synthesis of N-substituted and N-quaternized PBIs wherein $R_1$ and $R'$ are selected independently from unsubstituted or substituted alkyl(C1-C25) or aryl (C5-C25) or aralkyl (C5-C25) of polyaromatic hydrocarbons.

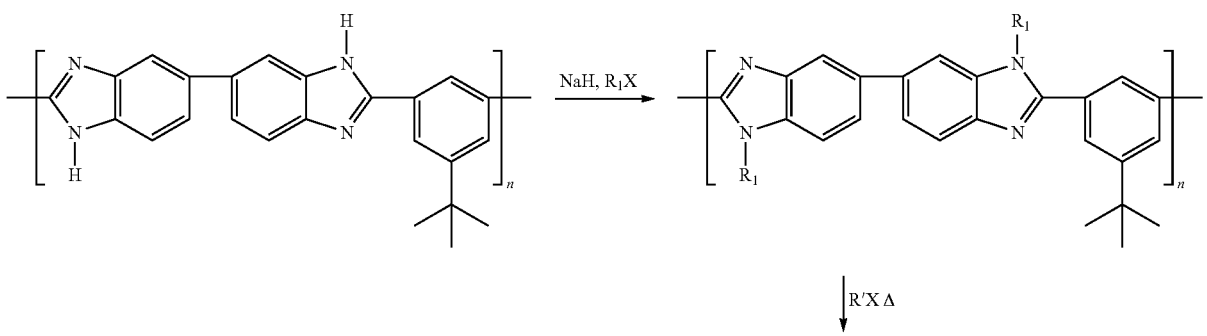

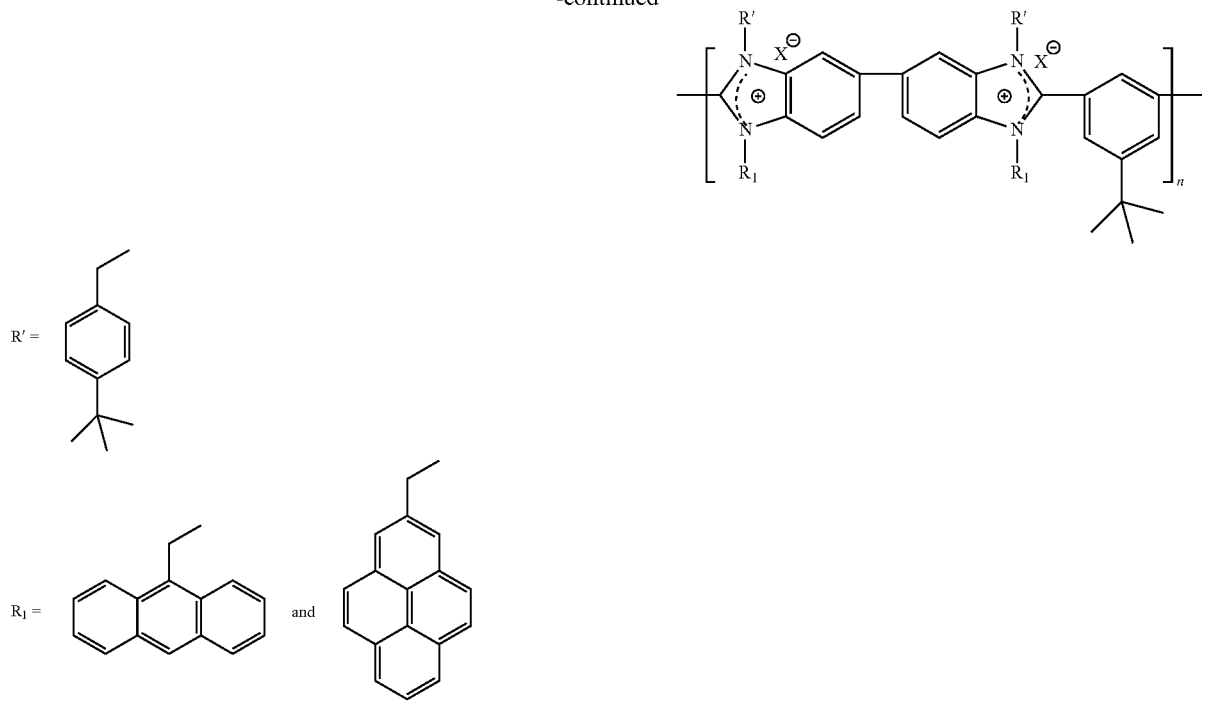

The polyaromatic hydrocarbons used in step (b) are selected from coronene, perylene, anthracene, phenanthrene, chrysene, pentacene, pentaphene, tetraphene, naphthalene, ovalene, rubrene and the like.

The aralkyl halide of polyaromatic hydrocarbon is preferably selected from 9-(chloromethyl)anthracene (An) or 2-(bromomethyl)pyrene (Py).

The present invention discloses a process for preparing PBI polymer comprising:

a. Heating polyphosphoric acid with stirring under constant flow of nitrogen followed by addition of 3,3'-diaminobenzidine and isophthalic acid or 5-tert-butylisophthalic acid to obtain the reaction mixture;

b. Increasing the temperature and maintaining it depending on the dicarboxylic acid to obtain the polymer by precipitating the formed solution into water followed by work-up.

The above process is shown below in Scheme 2:

Scheme 2: Synthesis of PBI wherein Ar is alkyl, aryl, substituted alkyl or substituted aryl.

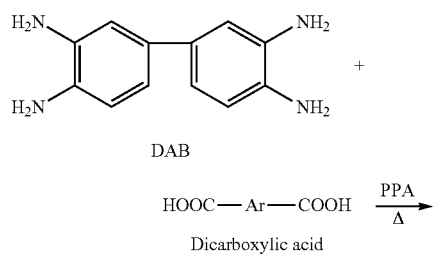

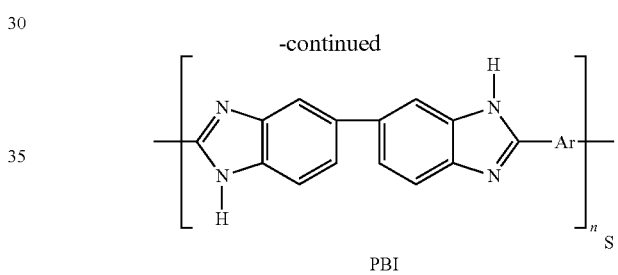

In a preferred embodiment, the dicarboxylic acid is isopthalic acid or tert-butylisophthalic acid.

The present invention discloses a process for preparing ABPBI polymer comprising stirring the reaction mixture containing 3, 4-diaminobenzoic acid (DABA) in PPA to obtain the polymer.

The stable fluorescent PIL composition based on PBI or ABPBI and its derivatives or analogues thereof exhibited enhanced florescence by excimer emission of around 480 nm and 510 nm for PBI-An, PBI-py respectively indicating the strong interactions of the excited anthracene and pyrene moieties with those in their ground states.

The invention discloses dense films of PILs, comprising PILs in the range of 0.1-3% w/v.

To study solid state quenching, the PIL films are prepared by a solution-casting method, using 0.5-3% (w/v) solution in N,N-dimethyl acetamide (DMAc) at 80° C. for 18 h under dry conditions.

The self-standing PIL films of the present invention were evaluated for fluorescence quenching by nitro aromatics (NACs) as well as possible interferents of different nature. The films exhibited rapid and selective fluorescence quenching when exposed to the saturated vapors of NACs at ambient temperature and pressure. Fluorescence emission of PIL films was affected little by the presence of commonly found interferents. Thus, this property of PIL allows for constructing a working device for explosive vapor detection in presence of interfering agents. Furthermore, fluorescence intensity could be recovered after the quenching, enabling the reuse of these PIL films for detection of NACs.

Figure 10:
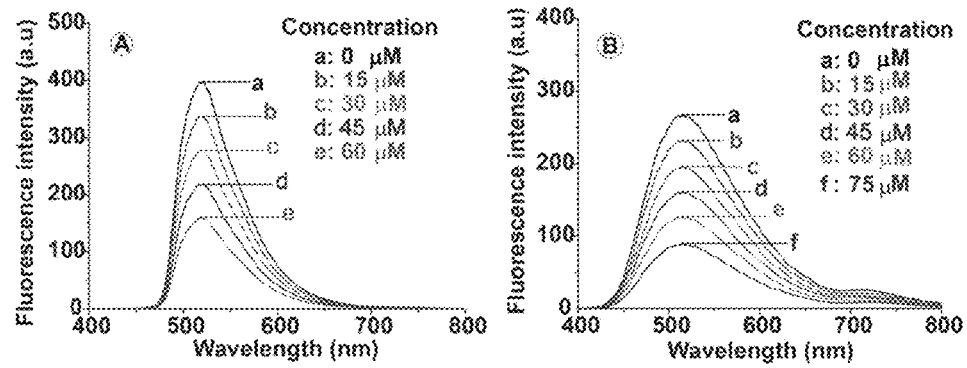
FIG. 10 Fluorescence quenching spectra of PILs A: [DPyDBzPBI-BuI][Br], B: [DAnDBzPBI-BuI][Br] in the presence of different concentrations of TNT in DMSO ($\lambda_{ex}$=350 nm). The intensity decreased with the increase in concentration of TNT. The Stern-Volmer binding constants for TNT were calculated to be $K_{sv}$=2.50×10$^4$ M$^{-1}$ ([DPyDBzPBI-I][Br]), $K_{sv}$=1.88×10$^4$ M$^{-1}$ ([DAnDBzPBI-I][Br]).
Figure 11:
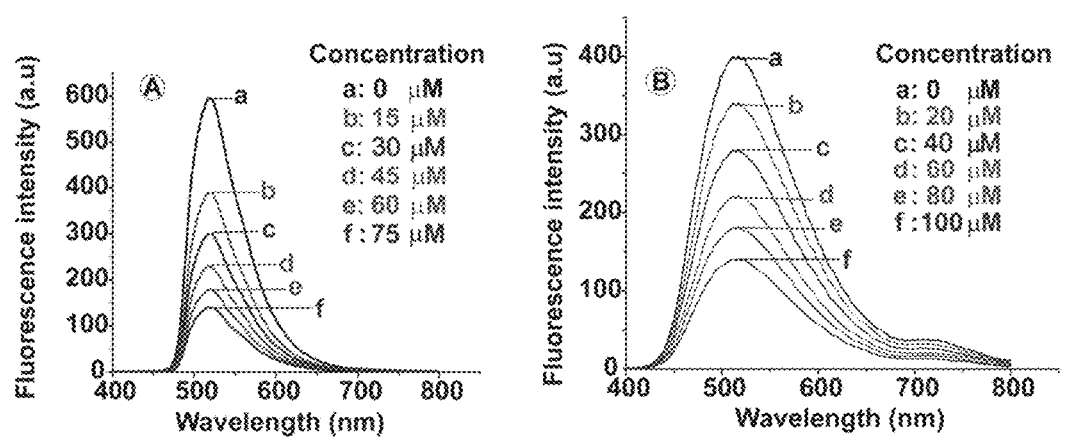
FIG. 11 depicts Fluorescence quenching spectra of PILs A: [DPyDBzPBI-BuI][Br], B: [DAnDBzPBI-BuI][Br] in the presence of different concentrations of PA in DMSO ($\lambda_{ex}$=350 nm). With an increase in concentration of PA, a decrease in intensity was as observed in earlier cases of NB and TNT. The Stern-Volmer binding constants for PA were calculated to be $K_{sv}$=3.25×10$^4$ M$^{-1}$ ([DPyDBzPBI-I][Br]), $K_{sv}$=2.03×10$^4$ M$^{-1}$ ([DAnDBzPBI-I][Br]).
Figure 12:
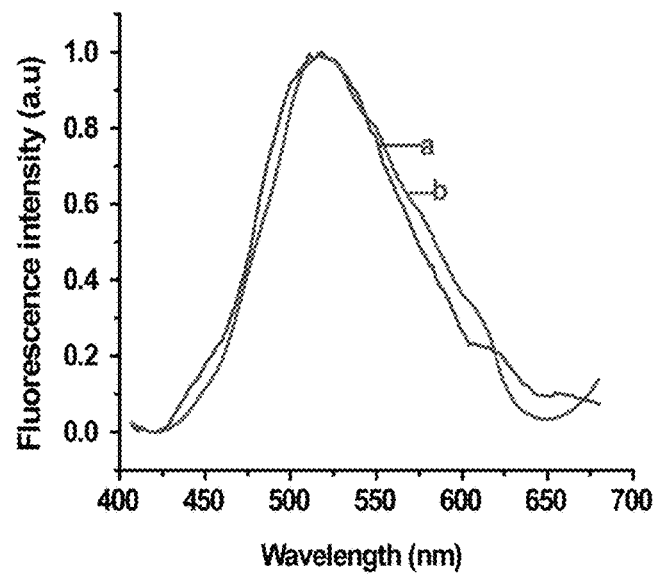
FIG. 12 depicts Fluorescence quenching spectra of a: [DPyDBzPBI-BuI][Br] and b: [DAnDBzPBI-BuI][Br] in film form (~12 μm thick). Transforming PIL into a thin film form did not shift its emission wavelength than observed in the solution state (given in FIG. 4 of the manuscript).

The present invention relates to Fluorescence Quenching of PIL's in solution. Accordingly, stock solution ($1.0 \times 10^{-5}$ M) of the PILs was placed in a quartz cell of 1 cm width and quenchers ($20 \times 10^{-6}$ M) solution selected from nitro aromatics such as 2,4,6 trinitrotoluene (TNT), picric acid (PA) and nitrobenzene (NB) were added gradually in an incremental fashion. Their corresponding fluorescence emission spectra were recorded at 298 K. For all measurement, PILs were excited at $\lambda ex=350$ nm and their corresponding emission wavelength was monitored from $\lambda ex=350$ nm. Both excitation and emission slit width were 1 nm for all the measurement. Relative fluorescence intensities were measured for solution of PILs in DMSO and analytes (PA, TNT and NB) were used as quenchers in DMSO. Analysis of the normalized fluorescence emission intensity (I0/I) as a function of increasing quenchers concentration ([Q]) was well described by the Stern-Volmer equation $(I0/I)-1=Ksv \times [Q]$. The Stern-Volmer binding constant was calculated from the slope of the Stern-Volmer plot3 and is indicated in FIGS. 10, 11 and 12 respectively.

Figure 13:
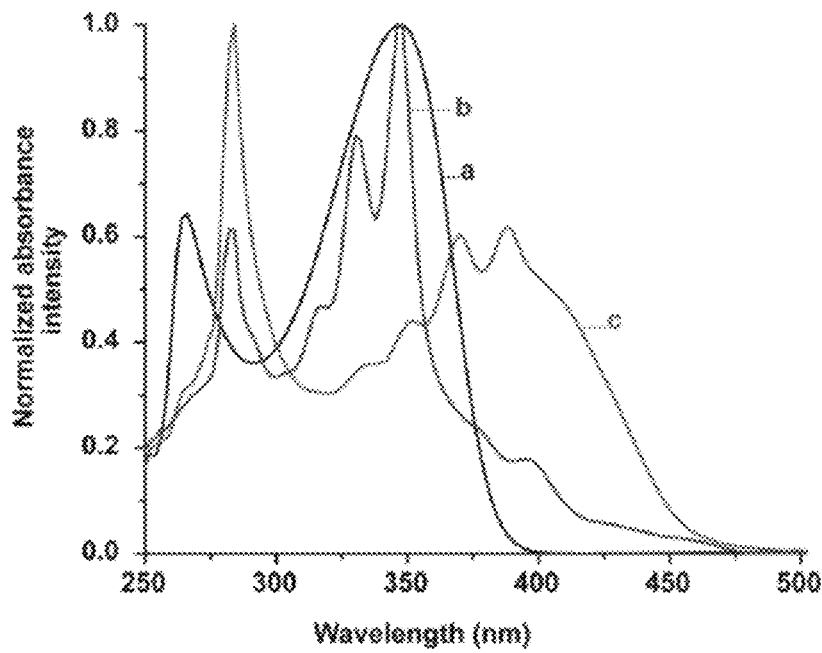
FIG. 13 depicts UV-visible spectra of (a) PBI-BuI, (b) [DPyDBzPBI-BuI][Br] and (c) [DAnDBzPBI-BuI][Br].

The present invention relate to Fluorescence Quenching of PIL's in solid state. The solid film-based sensing is more convenient means of analyte detection than solution state, as the detection of explosives may be required to detect in a hidden improvised explosive device or landmines. Accordingly, the PIL films were prepared by solution casting method using 0.5% (w/v) DMAc solution at 80° C. for several hours under dry conditions. After evaporation of the solvent, formed thin film was peeled off from the glass plate and kept in the vacuum oven at 80° C. for a week in order to ensure complete removal of the solvent. For quenching, a desiccator was used, in which a petri-dish that contained the analyte was placed. The polymer film was introduced in a desiccator after about 30 min (FIG. 13)

Figure 8:
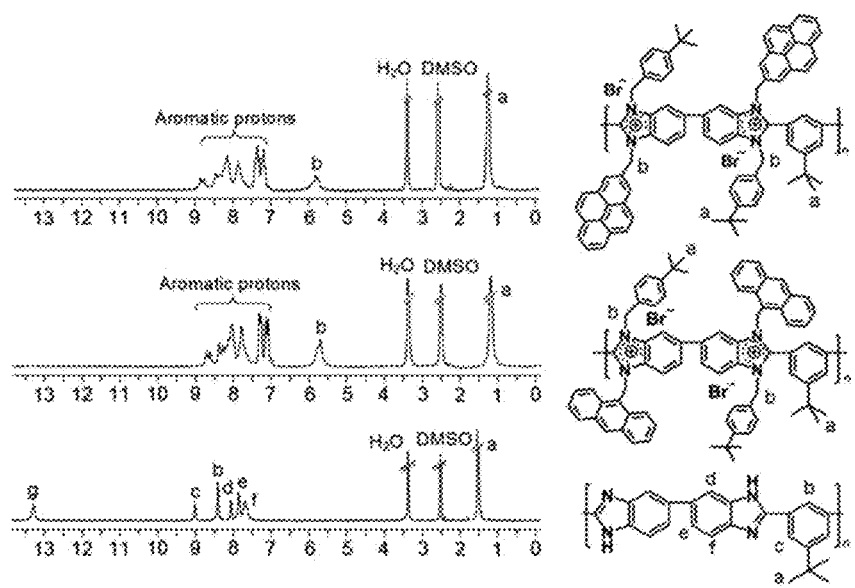
FIG. 8 depict $^1$H-NMR spectra of polymeric ionic liquids (PILs).

The fluorescence emission of PIL was observed to be sensitive to the presence of electron-deficient nitro aromatics. FIG. 7 and FIG. 8 depicts the fluorescence emission spectra of the polymer solution in DMSO at various concentrations of nitro aromatics. It was observed that nearly 70% of the emission was quenched when nitrobenzene concentration reaches 90 μmol/L.

Figure 14:
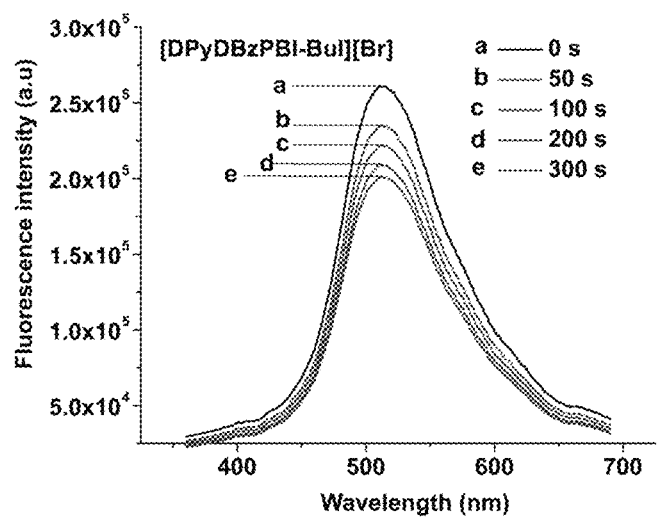
FIG. 14 depicts the fluorescence quenching of thick film (~40 μm) of pyrene containing PIL by NB. The quenching after 50 s exposure time was calculated to be 11%; while it was 30% after 300 s.

The present invention discloses significant change in UV-absorption and fluorescence properties in parent PBI-BuI due to the covalent attachment of pyrene and anthracene moieties in PILs. Strong UV-absorption band was observed at 347 nm (FIG. 14) due to the presence of benzimidazole group. The pyrene containing PIL, [DPyDBzPBI-BuI][Br] exhibited strong absorption bands at 347, 330 and 282 nm (FIG. 14), which could be correlated with the vibration bands of pyrene. On the other hand, anthracene containing PIL, [ADAnDBzPBI-BuI][Br] showed a wider UV absorption in the range 340-420 nm which correlate with the vibrational characteristic of isolated anthracene chromophore. (FIG. 14)

The fluorescent PIL composition of the present invention has high glass transition temperature. The self-standing fluorescent PIL films of the present invention exhibit stability towards high pressure for performing gas separation at elevated pressures and temperature and hence can be used as membranes in gas permeation for gases selected from He, H2, N2, CO2 and CH4.

The fluorescent PIL composition of the present invention is useful as explosive sensors, as chemo sensors and as membranes in gas permeation (as shown below in Table 2).

The present invention provides a method for detection of explosives comprising providing a device with fluorescent PIL film for explosive vapor detection in presence of interfering agents.

The present invention provides film-forming polymeric ionic liquids (PILs) possessing bright excimer emission tendency originating from pyrene and anthracene fluorophores present on their each repeat unit. Further, the invention provides advantageously an efficient and easy way of incorporation of polycyclic aromatic hydrocarbons, preferably, pyrene and anthracene fluorophores possessing high fluorescence quantum yield into a film-forming polymer. The present approach of post-modification of PBI allows the polymer PBI or ABPBI molecular weight to be independently optimized. The synthesized PILs show instant response to the explosives in solution as well as in vapor phase.

Further, the film forming polymeric ionic liquids regain the initial fluorescence intensity over repeated cycles indicating the high stability of the PILs.

EXAMPLES

Following examples are given by way of illustration and therefore should not be construed to limit the scope of the invention.

Example 1

Synthesis of Polybenzimidazole

A three-neck round bottom flask equipped with a mechanical stirrer, nitrogen inlet and an outlet was charged with 450 g of polyphosphoric acid and heated with stirring above 100° C. under constant flow of nitrogen. 15 g (0.07 mol) of 3,3'-diaminobenzidine and 11.63 g (0.07 mol) of isophthalic acid or 15.56 g (0.07 mol) of 5-tert-butyl-isophthalic acid was added to the reaction mixture. The temperature was slowly raised to 200° C. and maintained for 10-14 h, depending on the dicarboxylic acid. The polymer was obtained by precipitating the formed solution into water. The precipitated polymer was washed with water, followed by aqueous sodium bicarbonate and water. The obtained polymer was dried at 80° C. under vacuum. Similarly, PBI-I can be synthesized from Isophthalic acid and 3,3'-Diaminobenzidine in presence of polyphosphoric acid by the process described in example 1.

Example 2

Synthesis of Poly (2, 5-benzimidazole) (ABPBI)

The reaction mixture containing 5 g 3,4-diaminobenzoic acid (DABA) in 100 g PPA was stirred at 170° C. for an hour and then at 200° C. for an additional hour. Formed polymer after precipitating in water was crushed and washed with water till to get neutral pH. It was then kept in 10% NaOH for 16 h, washed with water to get neutral pH, soaked in acetone for 5 h and dried at 100° C. under vacuum for 3 days. ABPBI (Table 1) was used as such for further reactions of N-quaternization.

Example 3

N-Substitution of Polybenzimidazole

To a three-necked round bottom flask equipped with $N_2$ balloon and a septum, was charged 300 ml of dry DMSO, 1 gm of PBI, 2.1 equivalents of NaH and stirred at ambient temperature for 24 h. The reaction mixture was further heated at 80° C. for 3 h. At this stage, a deep blood red colour developed after the complete dissolution of PBI. The solution was allowed to cool to ambient and 2.1 molar equivalents of aralkyl iodide or (1-(bromomethyl)pyrene or 9-(Chloromethyl)anthracene dissolved in 10 ml of dry DMSO was added in a drop wise manner for a period of 15 minutes. The reaction mixture was precipitated indicating formation of N-substituted PBI. The reaction mixture was stirred further at ambient temperature for 12 h and was slowly poured on to the stirred water. The precipitated polymer was washed several times with water and dried in vacuum oven at 100° C. for a week.

Example 4

N-Substitution of ABPBI

To a three-necked round bottom flask equipped with N2 balloon and a septum, was charged 300 ml of dry DMSO, 1 gm of ABPBI, 2.1 equivalents of NaH and stirred at 170° C. for 5 h. A deep brown color developed yielding viscous homogeneous solution. To the mixture was added 1 molar equivalent of aralkyl halide or (1-(bromomethyl)pyrene or 9-(Chloromethyl)anthracene at 40° C. The reaction mixture was precipitated indicating formation of N-substituted ABPBI. The reaction mixture was stirred further at ambient temperature for 12 h and was slowly poured on to the stirred water. The precipitated polymer was washed several times with water and dried under vacuum.

Example 5

N-Quaternization of Polybenzimidazole

To a 3-necked round bottom flask was charged with 300 ml of dry DMSO, 1 gm of N-substituted PBI, 2.5 equivalents of 4-tert-butylbenzyl bromide and stirred under dry $N_2$ atmosphere at ambient for 12 h. The reaction mixture was further heated at 80° C. for 12 h. After attaining ambient temperature polymer was precipitated in a mixture of toluene and acetone (1:1). Obtained golden yellow fibrous precipitate was dried at 80° C. for 24 h. It was further purified by dissolving in DMSO and re-precipitating in toluene: acetone 1:1 mixture. Obtained precipitate was dried at 60° C. for 24 h and then in vacuum oven at 80° C. for 3 days. It was stored in dessicator until use.

Example 6

N-Quaternization of ABPBI

To a 3-necked round bottom flask was charged with 300 ml of dry DMSO, 10 gm of N-substituted ABPBI, 1.2 equivalents of 4-tert-butylbenzyl bromide and stirred under dry $N_2$ atmosphere at ambient for 12 h. The reaction mixture was further heated at 80° C. for 12 h. After attaining ambient temperature polymer was precipitated in a mixture of toluene and acetone (1:1). Obtained golden yellow fibrous precipitate was dried at 80° C. for 24 h. It was further purified by dissolving in DMSO and re-precipitating in toluene: acetone 1:1 mixture. Obtained precipitate was dried at 60° C. for 24 h and then in vacuum oven at 80° C. for 3 days. It was stored in desiccator until use.

Example 7

Synthesis of PBI-BuI

PBI-BuI was synthesized by polycondensation reaction of DAB (3,3'-diaminobenzidine) and 5-tert-butyl isophthalic acid as reported earlier.[1] A three-necked round bottom flask equipped with a mechanical stirrer, $N_2$ inlet and $CaCl_2$ drying tube was charged with 600 g of PPA (polyphosphoric acid), 20 g (0.18668 mol) of DAB and temperature was elevated to 140° C. After dissolution of DAB, 0.09334 mol of 5-tert-butyl isophthalic acid (20.743 g) was added; temperature was raised to 170° C. and maintained for 5 h under constant flow of $N_2$. The temperature was further raised to 200° C. and maintained for 12 h. The polymer was obtained by precipitation in water. It was crushed, washed thoroughly with water, kept in 10% $NaHCO_3$ for 16 h; followed by water wash. It was soaked in acetone for 16 h and dried in vacuum oven at 100° C. for 3 days. Further purification by dissolving in DMAc (3% w/v) and reprecipitation in water yielded yellow colored fibrous polymer (yield of purified polymer=98%). The inherent viscosity ($\eta_{inh}$) was determined at the polymer concentration of 0.2 g/dL in $H_2SO_4$ at 35° C. It was found to be 1.4 dL/g.

Example 8

Synthesis of Polymeric Ionic Liquids (PILs)

The N-substitution of PBI was carried out in dry DMSO by preparing sodium salt of PBI-BuI, followed by addition of the aralkyl halide. Typically a three-necked round bottom flask equipped with $N_2$ balloon and a septum was charged with 300 mL of dry DMSO, 10 g of PBI-BuI, 2.1 equivalents of NaH and stirred at ambient temperature for 24 h. The reaction mixture was then heated at 80° C. for 3 h. At this stage, a deep blood red color developed after the complete dissolution of PBI-BuI. The solution was allowed to cool to the ambient temperature and 2.1 molar equivalents of aralkyl halide, either 9-(chloromethyl)anthracene (An) or 2-(bromomethyl)pyrene (Py) dissolved in 10 mL of dry DMSO was added in a dropwise manner over a period of 15 minutes. The reaction mixture was precipitated indicating formation of the N-substituted PBI-BuI. The reaction mixture was stirred further at the ambient temperature for 12 h in order to allow complete dissolution and then was slowly poured into the stirred water. The precipitated polymer was washed several times with water and dried in a vacuum oven at 100° C. for 7 days.

The N-quaternization of thus obtained N-substituted PBI-BuI was carried out using 4-tert-butylbenzyl bromide (Bz). Typically, to a 3-necked round bottom flask, were charged 300 mL of dry DMSO, 10 g of N-substituted PBI-BuI, 2.5 equivalents of 4-tert-butylbenzyl bromide and the reaction mixture stirred under dry $N_2$ atmosphere at the ambient temperature for 12 h. The reaction mixture was further heated at 80° C. for 12 h. After attaining ambient temperature, the obtained polymer was precipitated in a mixture of toluene and acetone (1:1 v/v). The golden yellow fibrous precipitate was dried at 80° C. for 24 h. It was further purified by dissolving in DMF and reprecipitating in the toluene: acetone (1:1 v/v) mixture. Obtained polymer after vacuum drying was purified by dissolving in DMF and reprecipitation in the mixture of toluene and acetone (1:1). The yield of this reaction was 94%. The inherent viscosity ($\eta_{inh}$) of PILs was determined at the polymer concentration of 0.2 g/dL in DMSO at 35° C. It was found to be 3.3 dL/g for [DPyDBzPBI-BuI][Br] was, while for [DAnDBzPBI-BuI][Br] it was 3.1 dL/g.

Example 9

Estimation of Degree of Quaternization by Volhard's Method

Bromide present in formed PILs was determined by Volhard's method,[2] in which 0.1 g of polymer in powder form was stirred in 25 mL of 0.01M $AgNO_3$ solution for 24 h. Excess of unreacted $AgNO_3$ was titrated with 0.01 M KSCN to deduce the amount of $AgNO_3$ consumed with bromide present in the polymer.

Figure 9:
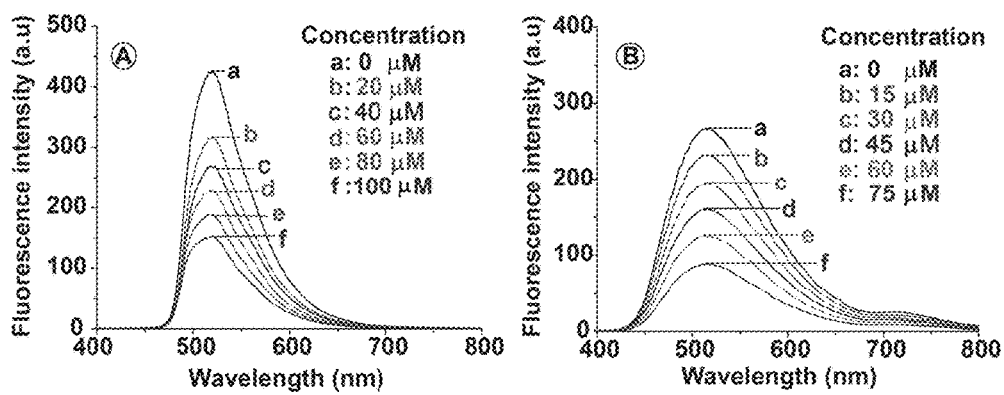
FIG. 9 Fluorescence quenching spectra of PILs A: [DPy-DBzPBI-BuI][Br], B: [DAnDBzPBI-BuI][Br] in the presence of different concentrations of nitrobenzene in DMSO ($\lambda_{ex}$=350 nm). This figure shows that with increase in the concentration of analyte, there is no change in the nature of emission spectra, except a gradual decrease in emission intensity. The Stern-Volmer binding constants for NB were calculated to be $K_{sv}$=1.78×10$^4$ M$^{-1}$ ([DPyDBzPBI-I][Br]), $K_{sv}$=1.59×10$^4$ M$^{-1}$ ([DAnDBzPBI-I][Br]).

FIG. 9 shows the $^1$H-NMR spectra of polymeric ionic liquids (PILs). The absence of a broad peak in the range of δ 13-14 (ascribed to imidazole N—H in the case of unsubstituted PBI-BuI) indicated that N-substitution reaction has quantitatively occurred.

Example 10

The dense films of PILs as prepared in eg 8 were prepared by a solution-casting method using their 0.5% (w/v) DMAc solution at 80° C. for 18 h under dry conditions. After evaporation of the solvent, the formed film (12 mm thick) was peeled off from the glass plate and dried in a vacuum oven at 80° C. for 7 days to ensure complete removal of the solvent. The minimum thickness achievable for present polymers by this method of film preparation was 12 mm. Such films were used for quenching studies.

Example 11

Optical Properties

FIGS. 1-6 show the fluorescence excitation and emission spectra (photoluminescence) of the precursor PBI, Pyrene functionalized PBI (PBI-py) and anthracene (PBI-An) functionalized PBI recorded in DMSO. The normalized absorption spectra of these polymers showed characteristic bands of anthracene and pyrene with no observed broadening and red shift relative to the bare anthracene and pyrene.

In complete contrast, the fluorescence emission spectra of these two polymers (PBI-An and PBI-py) were quite different. Although PBI showed no significant change in the emission wavelength, an excimer emission around 480 nm and 510 nm was observed for PBI-An, PBI-py respectively indicating the strong interactions of the excited anthracene and pyrene moieties with those in their ground states.

It is known in the literature that at low pyrene and anthracene concentration (several orders of $10^{-5}$M) monomer emission is dominant and no excimer emission is observed because of π stacking. However, at high concentrations of pyrene and anthracene, an excimer complex formation is feasible where the intermolecular interaction of excited pyrene and anthracene molecules with the ground state structures gives a green and blue emission respectively Similar fluorescence emissions were observed with PBI-Py and PBI-An indicating the incorporation into polymers which serves to effectively increase the local pyrene and anthracene concentration.

A comparison of photoluminescence demonstrated more intense light emission by PBI attached with pyrene than with anthryl group, which may be due to higher excimer formation tendency of pyrene.

Example 12

Fluorescence Quenching Studies with Nitroaromatics (Explosives)

The fluorescence emission of [DPyDBzPBI-BuI][Br] was sensitive to the presence of electron-deficient nitro aromatics. FIG. 7 and FIG. 8 depict the fluorescence emission spectra of the polymer solution in DMSO at various concentrations of nitro aromatics. It was observed that nearly 70% of the emission was quenched when nitrobenzene concentration reaches 90 μmol/L.

Example 13

Fluorescence Quenching Study in Solution

A 2 mL stock solution ($1.0 \times 10^{-5}$ M) of the PILs was placed in a quartz cell of 1 cm width and quenchers ($20 \times 10^{-6}$ M) solution was added gradually in an incremental fashion. Their corresponding fluorescence emission spectra were recorded at 298 K. For all measurement, PILs were excited at $\lambda_{ex}$=350 nm and their corresponding emission wavelength was monitored from $\lambda_{ex}$=350 nm. Both excitation and emission slit width were 1 nm for all the measurement. Relative fluorescence intensities were measured for solution of PILs in DMSO and analytes i.e. picric acid (PA), 2,4,6 trinitro toluene (TNT) and nitrobenzene (NB) were used as quenchers in DMSO. Analysis of the normalized fluorescence emission intensity ($I_0/I$) as a function of increasing quenchers concentration ([Q]) was well described by the Stern-Volmer equation $(I_0/I)-1=K_{sv} \times [Q]$. The Stern-Volmer binding constant was calculated from the slope of the Stern-Volmer plot[3] (FIG. 10, FIG. 11 and FIG. 12)

Example 14

Solid-State Fluorescence Quenching Study

The PIL films were prepared by solution casting method using 0.5% (w/v) DMAc solution at 80° C. for 18 h under dry conditions. After evaporation of the solvent, formed thin film was peeled off from the glass plate and kept in the vacuum oven at 80° C. for a week in order to ensure complete removal of the solvent. For quenching, a desiccator of 3 lt capacity was used, in which a petri-dish that contained 5 mL of nitrobenzene was placed. The polymer film was introduced in a desiccator after about 30 min. The minimum thickness obtained is approx. 12 μm. (FIG. 13)

The examples 11 to 13 relating to fluorescent quenching thus illustrate the use of PIL for constructing a working device for explosive detection in presence of interfering agents.

Example 15

Gas Permeation

Variable volume method was used for the determination of gas permeability of composite membranes as reported earlier [SCK JMS 2006]. The upstream pressure used was 20 atm at 35° C., while permeate side was maintained at the atmospheric pressure in order to measure volume of permeated gas. Permeability of pure gases, viz., He, $H_2$, $N_2$, $CH_4$ and $CO_2$ were measured for membranes. Permeate side of the cell was connected to a calibrated glass capillary containing small mercury slug. The volume of permeated gas was measured by mercury slug displacement. The permeability was calculated using the equation given below:

$$P = J \cdot l / \Delta p$$

Where, J=Flux of gas ($cm^3 \cdot cm^{-2} \cdot s^{-1}$), l=thickness of the membrane (cm), $\Delta p$=pressure difference across the membrane (cm Hg), and P is permeability expressed in the, Barrer (1 Barrer=$10^{-10}$ $cm^3$ (STP) $cm \cdot cm^{-2} \cdot s^{-1} \cdot cm\ Hg^{-1}$). The permeation measurements were repeated with at least three different membrane samples and the data was averaged (Table 2). The ideal selectivity ($\alpha$) was calculated as the ratio of permeability of two gases.

TABLE 1

Abbreviations of synthesized PBI

| Tetraamine used | Diacid used | Polymer abbreviation |
|---|---|---|
| 3,3'-Diaminobenzidine | Isophthalic acid | PBI-I |
| 3,3'-Diaminobenzidine | 5-tert-butylisophthalic acid | PBI-BuI |
| | 3,4-Diaminobenzoic acid | ABPBI |

TABLE 2

Permeability coefficient (P)$^a$ and permselectivity ($P_A/P_B$) of PILs estimated at 20 atm.

| PILs | $P_{He}$ | $P_{H_2}$ | $P_{N_2}$ | $P_{CH_4}$ | $P_{CO_2}$ | $P_{He}/P_{N_2}$ | $P_{He}/P_{CH_4}$ | $P_{H_2}/P_{N_2}$ | $P_{H_2}/P_{CH_4}$ | $P_{H_2}/P_{CO_2}$ | $P_{CO_2}/P_{N_2}$ | $P_{CO_2}/P_{CH_4}$ | $P_{N_2}/P_{CH_4}$ |
|---|---|---|---|---|---|---|---|---|---|---|---|---|---|
| [DPyDBzPBI-BuI][Br] | 25.7 | 24.8 | 1.11 | 0.82 | 23.9 | 23.2 | 31.3 | 22 | 53.4 | 0.96 | 21.5 | 29.1 | 1.35 |
| [DPyDBzPBI-BuI][BF$_4$] | 32.1 | 29.8 | 1.32 | 0.92 | 30 | 24.3 | 34.9 | 23 | 61.9 | 1.01 | 22.7 | 32.6 | 1.43 |
| [DPyDBzPBI-BuI][Tf$_2$N] | 38.8 | 36.5 | 1.81 | 1.25 | 36.2 | 21.4 | 31.0 | 20 | 42.8 | 0.99 | 20.0 | 29.0 | 1.45 |
| [DAnDBzPBI-BuI][Br] | 16.6 | 15.3 | 0.62 | 0.49 | 15 | 26.8 | 33.9 | 25 | 46.8 | 0.98 | 24.2 | 30.6 | 1.27 |
| [DAnDBzPBI-BuI][BF$_4$] | 25.9 | 23.3 | 0.92 | 0.75 | 25.1 | 28.2 | 34.5 | 25 | 50.1 | 1.08 | 27.3 | 33.5 | 1.23 |
| [DAnDBzPBI-BuI][Tf$_2$N] | 29.7 | 28.7 | 1.43 | 1.04 | 30.9 | 20.8 | 28.6 | 20 | 49.4 | 1.08 | 21.6 | 29.7 | 1.38 |

$^a$Permeability expressed in Barrer [1 Barrer = $1^{-10}$ $cm^3$ (STP) · $cm/cm^2$ · s · cm Hg].

What is claimed is:

1. A stable polymeric ionic liquid (PIL) composition, comprising a polymer selected from the group consisting of N-substituted, N-quaternized polybenzimidazole (PBI) and N-substituted and N-quaternized phosphoric acid doped PBI (ABPBI), wherein the N-substituted and N-quaternized PBI has the following structure:

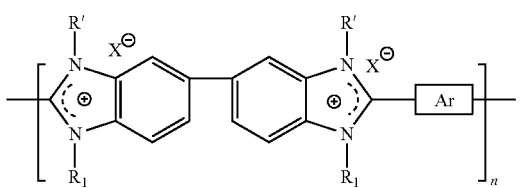

wherein $R_1$ and R' are independently selected from the group consisting of unsubstituted polyaromatic hydrocarbons and polyaromatic hydrocarbons substituted with alkyl(C1-C25) or aryl (C5-C25) or aralkyl (C5-C25),
wherein Ar is alkyl, aryl, substituted alkyl or substituted aryl, and
wherein $R_1$ and R' are fluorescing moieties.

2. A stable polymeric ionic liquid (PIL) composition according to claim 1, wherein $R_1$ and R' are substituted poly aromatic hydrocarbons.

3. The composition as claimed in claim 2, wherein the poly aromatic hydrocarbons are selected from the group consisting of coronene, perylene, anthracene, phenanthrene, chrysene, pentacene, pentaphene, tetraphene, naphthalene, ovalene, rubrene, and pyrene.

4. The composition as claimed in claim 2, wherein the poly aromatic hydrocarbons are pyrene or anthracene.

5. A stable polymeric ionic liquid (PIL) composition, comprising a polymer selected from the group consisting of N-substituted, N-quaternized PBI and N-substituted, N-quaternized ABPBI, covalently attached to a fluorescing moiety selected from poly aromatic hydrocarbons, wherein said composition is selected from the group consisting of;
    i. [DAnDBzPBI-BuI][Br] comprising PBI-BuI disubstituted with anthryl group quaternized with 4-tert-butylbenzyl bromide;
    ii. [DPyDBzPBI-BuI][Br] comprising PBI-BuI disubstituted with pyrenyl group quaternized with 4-tert-butylbenzyl bromide;
    iii. [DPyDBzPBI-I][Br] comprising PBI-I disubstituted with pyrenyl group quaternized with 4-tert-butylbenzyl bromide;
    iv. [AnBzABPBI][Br] comprising ABPBI substituted with anthryl group and quaternized with 4-tert-butylbenzyl bromide;
    v. [PyBzABPBI][Br] comprising ABPBI substituted with pyrenyl group and quaternized with 4-tert-butylbenzyl bromide; and
    vi. [DAnDBzPBI-I][Br] comprising PBI-I disubstituted with anthryl group quaternized with 4-tent-butyl benzyl bromide.

6. The composition as claimed in claim 5, wherein said composition is in the form of self-standing film in the range of 5-250 µM thickness.

7. A process for the preparation of stable PIL composition according to claim 5, comprising the steps of;
    a. preparing metal salt of PBI or ABPBI in dry solvent by known method followed by adding metal hydride to obtain a mixture;

b. heating the reaction mixture as obtained in step (a) at a temperature of about 80° C. until complete dissolution of polymer;
c. cooling the solution as obtained in step (b) followed by adding drop wise aralkyl halide of polyaromatic hydrocarbon dissolved in dry solvent to obtain precipitate of PIL composition;
d. N-quaternizing N-substituted PBI or ABPBI of step (C) to obtain a stable PIL composition.

8. The process according to claim 7, wherein the poly aromatic hydrocarbons are selected from coronene, perylene, anthracene, phenanthrene, chrysene, pentacene, pentaphene, tetraphene, naphthalene, ovalene, rubrene, and pyrene.

9. The process according to claim 8, wherein the poly aromatic hydrocarbons are pyrene or anthracene.

10. The polymeric ionic liquid (PIL) composition as claimed in claim 5, wherein said composition is useful as a sensor for detection of explosives, chemo sensors and as membranes in gas permeations.

11. The polymeric ionic liquid (PIL) composition as claimed in claim 1,
wherein

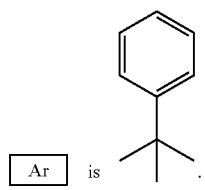

* * * * *